(12) United States Patent
Kim et al.

(10) Patent No.: US 10,390,707 B2
(45) Date of Patent: Aug. 27, 2019

(54) NEEDLE FOR BIOSENSOR AND BIO SENSOR INCLUDING THE SAME

(71) Applicant: Samsung Electronics Co., Ltd., Gyeonggi-do (KR)

(72) Inventors: Kwang-bok Kim, Incheon (KR);
Young-jae Oh, Gyeonggi-do (KR);
Seong-je Cho, Gyeonggi-do (KR);
Jae-geol Cho, Gyeonggi-do (KR);
Chul-ho Cho, Gyeonggi-do (KR);
Sun-tae Jung, Gyeonggi-do (KR);
Hyoung-seon Choi, Seoul (KR)

(73) Assignee: Samsung Electronics Co., Ltd (KR)

( * ) Notice: Subject to any disclaimer, the term of this patent is extended or adjusted under 35 U.S.C. 154(b) by 323 days.

(21) Appl. No.: 15/152,208

(22) Filed: May 11, 2016

(65) Prior Publication Data

US 2016/0331238 A1 Nov. 17, 2016

Related U.S. Application Data

(60) Provisional application No. 62/159,569, filed on May 11, 2015.

(30) Foreign Application Priority Data

Jun. 5, 2015 (KR) .......................... 10-2015-0080029

(51) Int. Cl.
*A61B 5/00* (2006.01)
*A61B 5/1459* (2006.01)

(52) U.S. Cl.
CPC .......... *A61B 5/0075* (2013.01); *A61B 5/1459* (2013.01); *A61B 5/443* (2013.01); *A61B 5/444* (2013.01); *A61B 5/6848* (2013.01); *A61B 2562/0233* (2013.01)

(58) Field of Classification Search
CPC ... A61B 5/0075; A61B 5/1459; A61B 5/6848; A61B 2562/0233
USPC ......................................................... 600/476
See application file for complete search history.

(56) References Cited

U.S. PATENT DOCUMENTS

| 5,280,788 | A | 1/1994 | Janes et al. |
| 7,343,188 | B2 * | 3/2008 | Sohrab ............... A61B 5/15146 600/345 |
| 8,615,281 | B2 * | 12/2013 | Yodfat .............. A61M 5/14248 600/310 |
| 9,675,789 | B2 * | 6/2017 | Chen .................... A61K 9/0021 |

(Continued)

FOREIGN PATENT DOCUMENTS

WO WO 2011/083111 7/2011

OTHER PUBLICATIONS

International Search Report dated Aug. 18, 2016 issued in counterpart application No. PCT/KR2016/004944, 13 pages.

(Continued)

*Primary Examiner* — Christopher A Flory
(74) *Attorney, Agent, or Firm* — The Farrell Law Firm, P.C.

(57) ABSTRACT

Disclosed is a biosensor needle including a light-transmissive main body having a width that is less than a length so as to be inserted into a testee, and a plurality of metal particles provided at at least a part of the main body and generating a surface enhanced Raman scattering (SERS) effect of light incident through the main body.

11 Claims, 18 Drawing Sheets

(56) References Cited

U.S. PATENT DOCUMENTS

| | | | |
|---|---|---|---|
| 2005/0113657 A1* | 5/2005 | Alarcon | G01N 21/7703 600/342 |
| 2008/0157421 A1* | 7/2008 | Mukai | A61H 39/086 264/164 |
| 2008/0198358 A1* | 8/2008 | Alarcon | G01N 21/7703 356/36 |
| 2011/0009807 A1* | 1/2011 | Kjeken | A61N 1/327 604/21 |
| 2011/0184259 A1* | 7/2011 | Alarcon | A61B 5/14532 600/316 |
| 2011/0188035 A1* | 8/2011 | Kuo | G01J 3/44 356/301 |
| 2011/0224515 A1* | 9/2011 | Mir | A61B 5/14532 600/317 |
| 2011/0319742 A1* | 12/2011 | Mir | A61B 5/14532 600/407 |
| 2012/0276549 A1* | 11/2012 | Cunningham | A61M 39/08 435/7.1 |
| 2012/0309080 A1* | 12/2012 | Cunningham | G01N 21/658 435/288.7 |
| 2013/0141719 A1 | 6/2013 | Furusho | |
| 2013/0168536 A1* | 7/2013 | Guo | G02B 1/005 250/216 |
| 2013/0338627 A1* | 12/2013 | Rylander | A61M 5/158 604/501 |
| 2014/0071447 A1 | 3/2014 | Naya et al. | |
| 2014/0099279 A1* | 4/2014 | Furst | A61K 31/436 424/85.1 |
| 2014/0107450 A1* | 4/2014 | Simpson | A61B 5/6848 600/365 |
| 2014/0211206 A1* | 7/2014 | Wang | G01N 1/00 356/300 |
| 2014/0213866 A1* | 7/2014 | Simpson | A61B 5/6848 600/345 |
| 2015/0289788 A1* | 10/2015 | Simpson | A61B 5/1473 600/345 |
| 2016/0089065 A1* | 3/2016 | Simpson | A61B 5/6848 600/347 |
| 2016/0089068 A1* | 3/2016 | Simpson | A61B 5/6848 600/347 |
| 2016/0113556 A1* | 4/2016 | Simpson | A61B 5/6848 600/347 |
| 2017/0095369 A1* | 4/2017 | Andino | A61M 5/3286 |
| 2018/0042529 A1* | 2/2018 | Simpson | A61B 5/1473 |

OTHER PUBLICATIONS

Dongmao Zhang et al., "Isotope Edited Internal Standard Method for Quantitative Surface-Enhanced Raman Spectroscopy", Analytical Chemistry, Jun. 1, 2005, 7 pages.

M. Sackmann et al., "Surface Enhanced Raman Scattering (SERS)—a Quantitative Analytical Tool?", Journal of Raman Spectroscopy, 2006, 6 pages.

David L. Stokes et al., "Development of an Integrated Single-Fiber SERS Sensor", Sensors and Actuators B 69, 2000, 9 pages.

Karen E. Shafer-Peltier et al., "Toward a Glucose Biosensor Based on Surface-Enhanced Raman Scattering", JACS Articles, American Chemical Society, 2003, 6 pages.

Joydeep Chowdhury et al., Concentration-Dependent Suface-Enhanced Resonance Raman Scattering of a Porphyrin Derivative Absorbed on Colloidal Silver Particles, Journal of Colloid and Interface Science 263, 2003, 9 pages.

Patrick D. O'Neal et al., Feasibility Study using Surface-Enhanced Raman Spectroscopy for the Quantitative Detection of Excitatory Amino Acids, Journal of Biomedical Optics 8(1), Jan. 2003, 7 pages.

* cited by examiner 100b 100a 100b 100a 100b 100a 100b 100a 100b 100a 100b 100a 100a 100b 100b 100a 100b 100b 100a 100b 100b 100a 100b 100b

NEEDLE FOR BIOSENSOR AND BIO SENSOR INCLUDING THE SAME

PRIORITY

This application claims priority under 35 U.S.C. 119(e) to a U.S. Provisional Patent Application filed in the U.S. Patent and Trademark Office on May 11, 2015 and assigned Ser. No. 62/159,569, and under 35 U.S.C § 119(a) to a Korean Patent Application filed in the Korean Intellectual Property Office on Jun. 5, 2015 and assigned Serial No. 10-2015-0080029, the contents of each of which are incorporated herein by reference.

BACKGROUND

1. Field of the Invention

The present disclosure relates generally to a biosensor, and more particularly, to a biosensor needle that is inserted into the skin of a living body to measure a biosignal, and a biosensor including the needle.

2. Description of the Related Art

Interest in medical apparatuses has increased along with public interest in health management issues, developments in medical science, and increase in the average lifespan. Accordingly, a range of medical apparatuses has expanded from conventional medical apparatuses used in hospitals or medical examination organizations to smaller medical apparatuses provided in portable medical apparatuses carried by individuals.

Active research and development has been performed on diagnostic equipment capable of easily obtaining a health state or other bioinformation of a user. To this point, however, the conventional art is lacking in such medical apparatuses that accurately and conveniently provide such information.

Accordingly, there is a need in the art for diagnostic equipment capable of accurately and conveniently obtaining biological (bio) information.

SUMMARY

The present disclosure has been made to address the above-mentioned problems and disadvantages, and to provide at least the advantages described below.

Accordingly, an aspect of the present disclosure is to provide a biosensor needle that is inserted into a testee to measure a biosignal, which improves reliability of a biosignal measured in the testee, and a biosensor including the biosensor needle.

According to an aspect of the present disclosure, a biosensor needle includes a light-transmissive main body having a width that is less than a length of the main body, and is insertable into a testee, and a plurality of metal particles provided on at least a portion of a surface of the main body and generating a surface enhanced Raman scattering effect of light incident through the main body.

According to another aspect of the present disclosure, a biosensor includes a light source, a main needle comprising a first main body insertable into a testee and that transfers incident light output from the light source to a skin of the testee, and a plurality of metal particles provided on at least a portion of a surface of the first main body and enhancing a spectrum signal of light reflected from the skin of the testee, and a measurement unit that measures a spectrum of the reflected light.

BRIEF DESCRIPTION OF THE DRAWINGS

The above and/or other aspects, features and advantages of the present disclosure will become apparent and more readily appreciated from the following description of the embodiments, taken in conjunction with the accompanying drawings in which.

DETAILED DESCRIPTION OF EMBODIMENTS OF THE PRESENT DISCLOSURE

Figure 1:
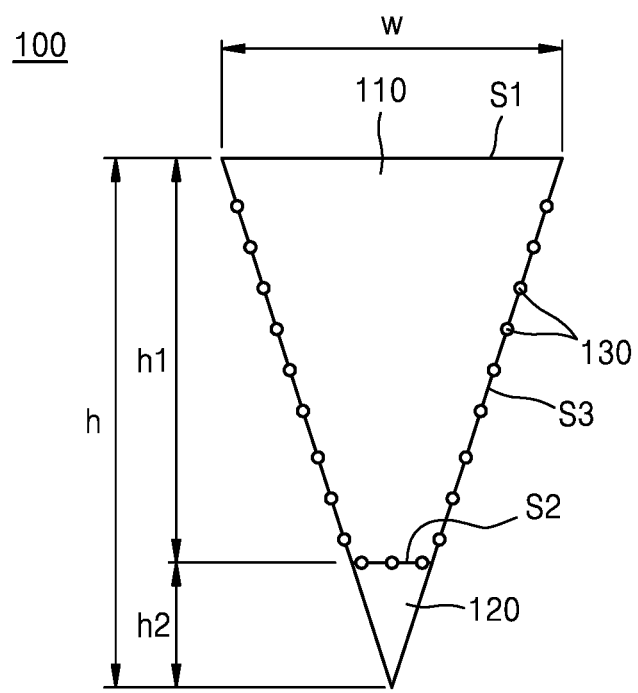
FIG. 1 is a cross-sectional view of a biosensor needle according to an embodiment of the present disclosure.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. A description of well-known functions and/or configurations will be omitted for the sake of clarity and conciseness.

The thickness or size of each layer illustrated in the drawings may be exaggerated for convenience of explanation and clarity. When a material layer (i.e., first layer) is described in the following description to exist on another layer (i.e., second layer), the first layer may exist directly on the second layer or a third layer may be interposed between the first and second layers.

In a layer structure, when a constituent element is disposed "above" or "on" another constituent element, the constituent element may be directly on the other constituent element or above the other constituent elements in a non-contact manner.

Terms such as "first" and "second" are used herein merely to describe a variety of constituent elements, but the constituent elements are not limited by the terms. The terms are used only for the purpose of distinguishing one constituent element from another constituent element.

An expression used in the singular form also encompasses the expression of the plural form, unless it has a clearly different meaning in the context. When a part "may include" a certain constituent element, unless specified otherwise, the part may not be construed to exclude another constituent element but may be construed to further include other constituent elements.

Terms such as "portion", "unit", "module", and "block" stated in the specification may signify a unit to process at least one function or operation and the unit may be embodied by hardware, software, or a combination of hardware and software.

FIG. 1 is a cross-sectional view of a biosensor needle 100 according to an embodiment of the present disclosure.

Referring to FIG. 1, the needle 100 includes a main body 110 that is light-transmissive and is inserted into a testee, and a plurality of metal particles 130 are provided on at least a part of the main body 110. The needle 100 includes a biodegradable layer 120 attached onto at least a part of a surface of the main body 110 and including a biodegradable polymer material. One end of the biodegradable layer 120 contacts the main body 110 and the other end of the biodegradable layer 120 has a sharp, pointed shape. Accordingly, the biodegradable layer 120 may be easily inserted into the testee. S1, S2 and S3 refer to surfaces of the main body 110, and will be described below at least in reference to FIG. 3.

The needle 100 has a length h, the main body has a length h1, and the biodegradable layer 120 has a length h2. Lengths h1 and h2 will be described below at least in reference to FIG. 2. A width W of the main body 110 is less than the length h1. Accordingly, the main body 110 may be easily inserted with the biodegradable layer 120 into the testee.

The above-described testee signifies a living body subject to a test, such as a human or an animal. An interior of the testee, into which the needle 100 is insertable, may signify internal tissues of a living body of the testee, such as inside skin tissue. When the testee is a human, the needle 100 is insertable into any one of epidermis, dermis, and a subcutaneous layer of skin tissue of the testee. A position where the needle 100 is inserted into the testee may be changed according to a target material to be measured. For example, when the testee is a human body, the needle 100 is insertable into an abdomen or a rear side of an arm. However, the present disclosure is not limited thereto, and the position where the needle 100 is inserted may vary.

Figure 2:
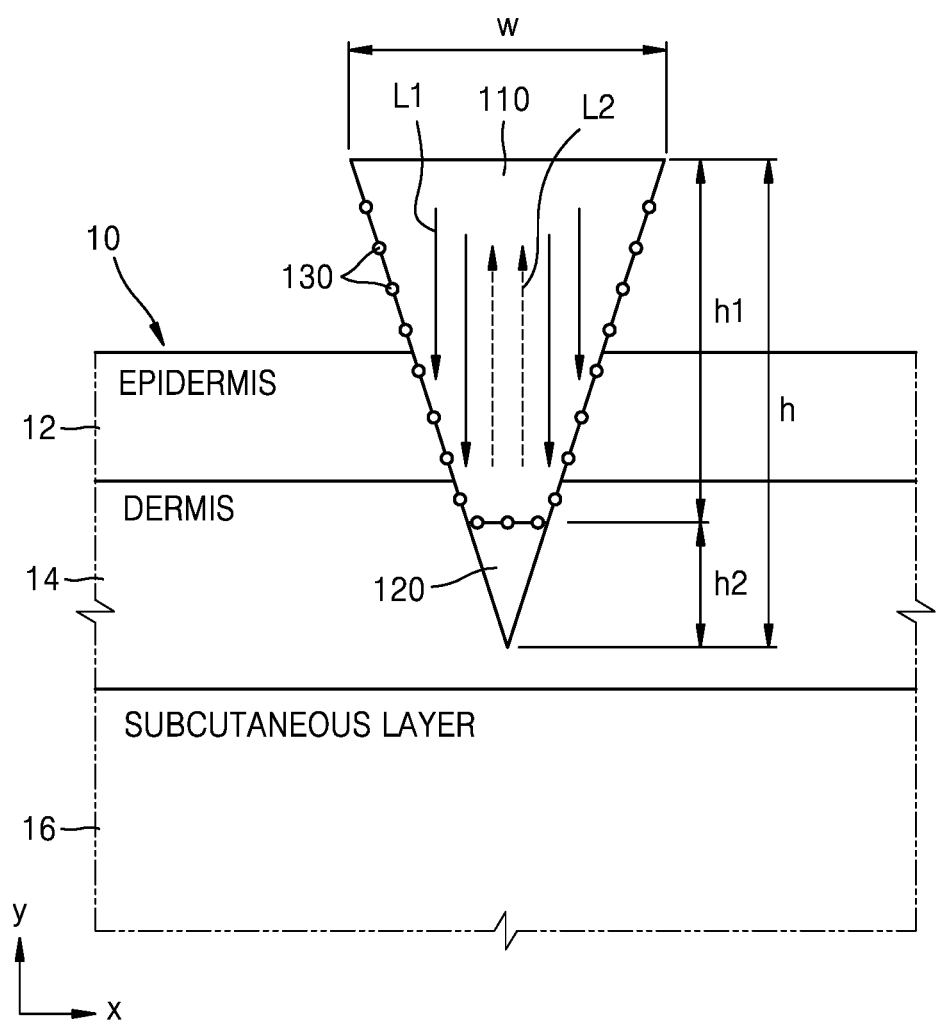
FIG. 2 is a cross-sectional view illustrating the biosensor needle of FIG. 1 inserted into a testee.

FIG. 2 is a cross-sectional view illustrating the needle 100 of FIG. 1 inserted into a testee.

Referring to FIG. 2, the needle 100 is inserted into the skin of a testee 10 at a depth that may vary. For example, the needle 100 is insertable into an area of a dermis 14 of the testee 10. Since the dermis 14 includes interstitial fluid (ISF) and a capillary vessel, a signal related to bioinformation of the testee 10 may be obtained from the dermis 14. In a human body, pain is minimally felt down to the dermis 14, and thus, even when the needle 100 is inserted down to the dermis 14, the needle 100 causes minimal pain to the testee 10. When a biosignal is measured at the dermis 14, a length h of the needle 100 is about 700 µm to about 1400 µm. In the needle 100, the length h1 of the main body 110 and the length h2 of the biodegradable layer 120 may vary according to a position where a biosignal is to be measured. However, when a biosignal is to be measured at the dermis 14, the length h2 of the biodegradable layer 120 is less than a thickness of the dermis 14, and the length h1 of the main body 110 is greater than at least a thickness of an epidermis 12. Accordingly, the length h1 of the main body 110 is about 70 microns (µm) to about 1400 µm. The length h2 of the biodegradable layer 120 is less than about 1330 µm. A width W of the main body 110 is about 50 µm so that the needle 100 may be easily inserted into the skin of the testee 10.

A depth range in which the dermis 14 is distributed in the testee 10 may vary according to an area of the testee 10. For example, in an abdomen of a human body, the thickness of an epidermis 12 is about 79.4 µm±33.9 µm, and the thickness of the dermis 14 is about 1248.4 µm±262.5 µm. In a rear side of a human arm, the thickness of the epidermis 12 is about 83.5 µm±36.2 µm and the thickness of the dermis 14 is about 1030.4 µm±327.8 µm. Accordingly, the main body 110 is inserted to a depth of about 70 µm to 1300 µm from a skin surface of the testee 10. When the main body 110 is inserted down to the dermis 14, a depth to which the main body 110 is inserted varies according to a position where the main body 110 is inserted.

In the description of FIG. 2, the needle 100 is described as being inserted down to an area of the dermis 14 of the testee 10. However, the present disclosure is not limited thereto. For example, the needle 100 may be inserted down to only the epidermis 12, in which case a length h of the needle 100 is about 70 µm. The needle 100 is insertable even into the subcutaneous layer 16 of the testee 10. In this case, the length h of the needle is greater than about 1400 µm.

In the needle 100 of FIG. 2, the biodegradable layer 120 decomposes inside the testee 10 by including a biodegradable polymer material such as at least one of polylactic acid, poly(lactic-co-glycolic) acid, poly(caprolactone), polyhydroxyalkanoates, polypropylene fumarate), polydioxanone, polyglycolide, polyanhydrides, polyacetals, poly(ortho esters), polycarbonates, polyurethanes, and polyphosphazenes. However, the biodegradable polymer materials are merely examples, and the present disclosure is not limited thereto.

The biodegradable polymer material may have a Raman shift value that is different from that of a material included in the below-described interstitial fluid or blood. Accordingly, even when the biodegradable polymer material has decomposed and mixed with the interstitial fluid or blood, spectrum signals of the materials included in the interstitial fluid or blood may not be affected.

Figure 3:
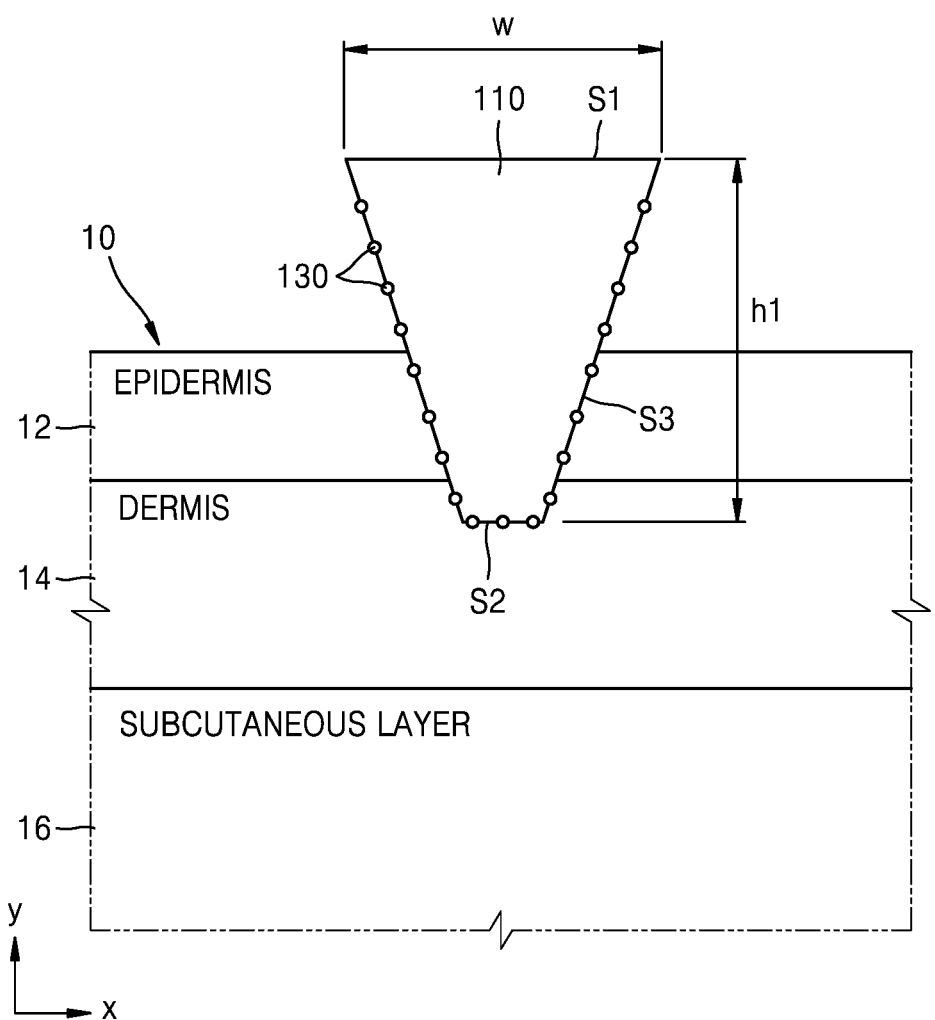
FIG. 3 is a cross-sectional view illustrating the biosensor needle of FIG. 2 after a biodegradable layer has decomposed.

FIG. 3 is a cross-sectional view illustrating the needle 100 of FIG. 2 after the biodegradable layer 120 has decomposed.

Referring to FIG. 3, the biodegradable layer 120 including a biodegradable polymer material has decomposed inside the skin of the testee 10. The main body 110 contacts the skin of the testee 10 when the biodegradable layer 120 has decomposed. Light may be incident upon an incident surface S1 of the main body 110. Incident light L1 may be transferred to the skin of the testee 10 through the main body 110. The main body 110 includes a transparent polymer material to transmit the incident light and a reflected light. The transparent polymer material may be obtained by polymerizing at least one monomer of aniline, EDOT (3,4-ethylenedioxythiophene), pyrrole, N-succinimidyl acrylate, acrylamide, thiophene, aniline-co-pyrrole, amylopectin, carboxymethyl cellulose (CMC), dialcohol dimethyl quaterthiophene-co-adipic acid (AMQAA), or methylvinylether/maelic anhydride+ethyleneglycol. However, the materials are not limited thereto. The main body 110 has a hollow shape.

The incident light L1 incident upon the main body 110 is reflected from the skin of the testee 10. A spectrum of light reflected from the skin of the testee 10 may be different from a spectrum of the incident light L1. In this state, the spectrum of the reflected light depends on the types and amounts of the materials included in the skin of the testee 10. Accordingly, once the spectrum of the reflected light is identified, a distribution of materials existing in the skin of the testee 10 may be identified. Information such as a health state of the testee 10, whether the testee 10 has a disease, or whether the testee 10 is on medication may be extracted from the distribution of materials existing in the skin of the testee 10.

FIG. 3 illustrates when the main body 110 contacts the dermis 14 of the testee 10. The main body 110 includes at least one surface S2 (hereinafter, perpendicular surface) that is substantially perpendicular to the length direction (y-axis) of the needle 100. The perpendicular surface S2 contacts the dermis 14 of the testee 10. In general, the strength of a Raman spectrum signal is at a maximum when a light reflection surface and a light incident direction are substantially perpendicular to each other, because a signal loss may be generated due to scattering when a light incident direction and a light reflection surface are askew with respect to each other. Accordingly, when the main body 110 has the perpendicular surface S2 that is substantially perpendicular to the length direction (y-axis) of the needle 100, as illustrated in FIG. 3, a spectrum signal strength reflected from the skin contacting the perpendicular surface S2 increases. The main body 110 includes a lateral surface S3 that is askew with respect to the length direction (y-axis) of the needle 100. Since the lateral surface S3 of the main body 110 contacts the skin of the testee 10, a spectrum signal may be obtained from the light reflected from the skin contacting the lateral surface S3 of the main body 110.

The spectrum of the light reflected from the surfaces S2 and S3 contacting the dermis 14 in the main body 110 depend on the distribution of the materials included in interstitial fluid or blood of capillary vessels included in the dermis 14 of the testee 10. Unlike the epidermis 12, since interstitial fluid and capillary vessels are distributed in the dermis 14, bioinformation extracted from the spectrum of the light reflected from the dermis 14 has higher reliability compared to bioinformation extracted from the spectrum of the light reflected from the epidermis 12. Since the main body 110 functions as an optical waveguide of the incident light L1 and the reflected light L2, noise due to scattering of a skin surface or interference materials in the skin is reduced. In other words, a biosignal obtained by the needle 100 according to an embodiment of the present disclosure has higher reliability compared to a biosignal obtained by conventional spectrum analysis methods.

The metal particles 130 in the main body 110 enhance a Raman spectrum signal of the light reflected from the skin of the testee 10, which is referred to as a surface enhanced Raman scattering (SERS) effect. When the SERS effect is generated by the metal particles 130, the strength of the Raman spectrum signal of the light reflected from the skin of the testee 10 is enhanced, and spectrum analysis from the enhanced Raman spectrum signal is easily performed.

In order to generate the above-described SERS effect, the metal particles 130 are provided on at least a part of the surface of the main body 110 contacting the skin of the testee 10. Although FIGS. 1 to 3 illustrate an example in which the metal particles 130 are uniformly provided on the surface of the main body 110, the present embodiment is not limited thereto. For example, a distribution density of the metal particles 130 may vary according to the surface of the main body 110. To allow only a Raman spectrum signal in a region of the dermis 14 to be selectively amplified, the metal particles 130 are provided only on the surface of the main body 110 contacting the dermis 14.

The size and arrangement distance d of the metal particles 130 may vary. For example, the diameter of each of the metal particles 130 may be around several nanometers to several micrometers. The distance d between the metal particles 130 may be less than about 150 nm. When the distance d between the metal particles 130 is decreased, the Raman spectrum signal may be relatively increased further. However, the above values are merely exemplary, and the present embodiment is not limited thereto. The metal particles 130 include at least one of gold (Au) particles, silver (Ag) particles, and copper (Cu) particles. The metals are merely exemplary, and the present embodiment is not limited thereto.

Since the metal particles 130 enhance the Raman spectrum signal, even when the width W of the main body 110 is decreased to around several tens of micrometers, a strong Raman spectrum signal may be obtained from the reflected light. As the size of the main body 110 decreases, pain the testee 10 feels when the needle 100 including the main body 110 is inserted into the testee 10 may be reduced.

Figure 4:
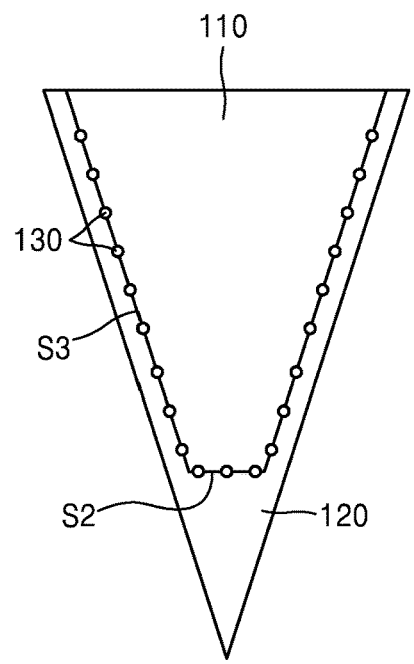
FIG. 4 is a cross-sectional view of a biosensor needle according to another embodiment of the present disclosure.

FIG. 4 is a cross-sectional view of the needle 100 according to another embodiment of the present disclosure.

In the description of the embodiment of FIG. 4, redundant descriptions related to FIGS. 1 to 3 are omitted. Referring to FIG. 4, the biodegradable layer 120 may extend to at least a part of the lateral surface S3 of the main body 110. Accordingly, the metal particles 130 provided on the surface of the main body 110 may be prevented from being detached while the main body 110 is inserted into the skin of the testee 10. The biodegradable layer 120 including a biodegradable polymer material decomposes when the needle 100 of FIG. 4 is inserted into the skin of the testee 10. After the biodegradable layer 120 has decomposed, the needle 100 of FIG. 4 contacts the skin of the testee 10 as illustrated in FIG. 3.

Figure 5:
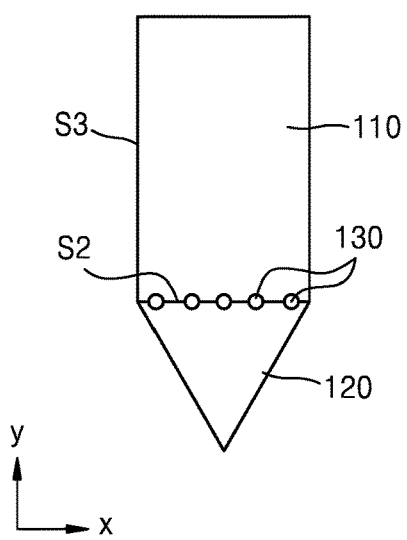
FIG. 5 is a cross-sectional view of a biosensor needle according to another embodiment of the present disclosure.

FIG. 5 is a cross-sectional view of the needle 100 according to another embodiment of the present disclosure.

Referring to FIG. 5, the main body 110 of the needle 100 has a column shape and includes the perpendicular surface S2 substantially perpendicular to the length direction (y-axis) of the needle 100. The metal particles 130 are provided at the perpendicular surface S2 of the main body 110. The lateral surface S3 of the main body 110 may be parallel to the length direction (y-axis) of the needle 100. The main body 110 of FIG. 4 may be relatively easily manufactured because the structure of the main body 110 of FIG. 4 is simpler than that of the main body 110 of FIG. 3. A spectrum signal may be obtained from the light reflected from the skin of the testee 10 contacting the perpendicular surface S2 of the main body 110. In this case, the perpendicular surface S2 and the incident light may be substantially perpendicular to each other. Accordingly, the Raman spectrum signal strength of the reflected light increases.

The biodegradable layer 120 has one end contacting the perpendicular surface S2 and the other end having a sharp pointed shape. Accordingly, the biodegradable layer 120 may be easily inserted into the skin of the testee 10. Since the biodegradable layer 120 is attached on the main body 110, even when the main body 110 does not have a sharp end, the main body 110 is inserted into the skin of the testee 10 with the biodegradable layer 120. Since the biodegradable layer 120 covers the perpendicular surface S2 where the metal particles 130 are arranged, in the main body 110, the metal particles 130 may not be detached from the perpendicular surface S2 of the main body 110 while the main body 110 is inserted into the testee 10.

Figure 6:
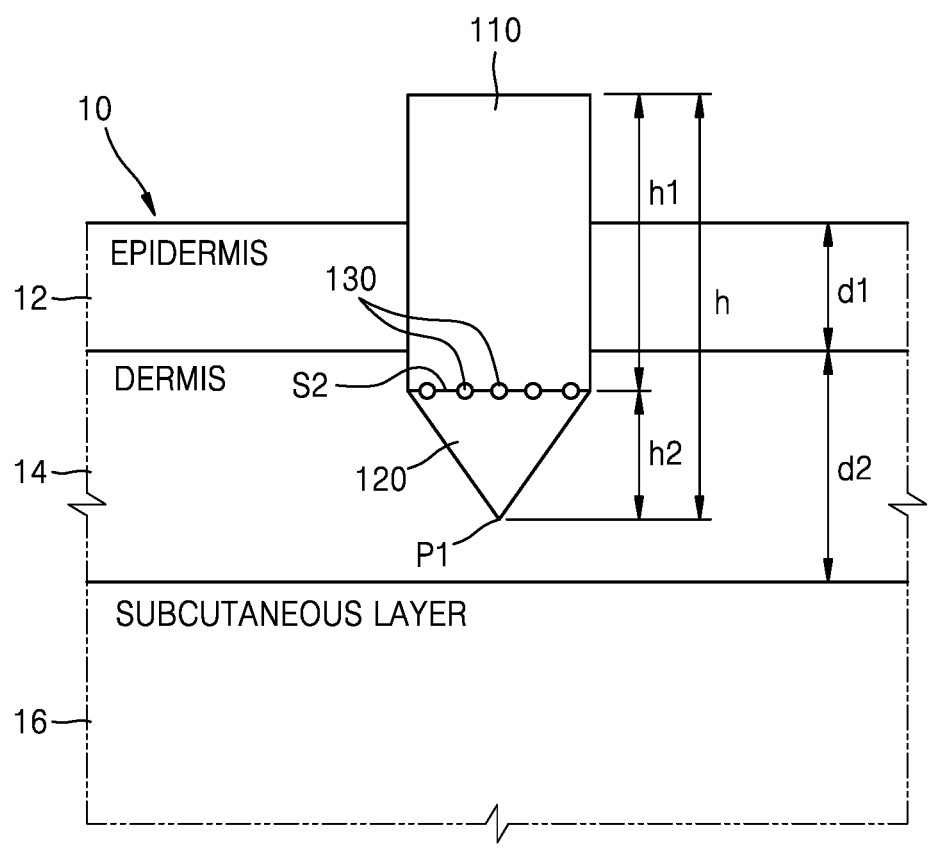
FIG. 6 is a cross-sectional view illustrating the biosensor needle of FIG. 5 inserted into a testee.

FIG. 6 is a cross-sectional view illustrating the needle 100 of FIG. 5 inserted into the testee 10.

Referring to FIG. 6, when the needle 100 is inserted into the skin of the testee 10, the perpendicular surface S2 that is substantially perpendicular to the length direction (y-axis) of the needle 100 in the main body 110 is located in the region of the dermis 14 and the light incident upon the main body 110 is reflected from the dermis 14. An end point P1 of the biodegradable layer 120 is located in the region of the dermis 14. Some pain may be inflicted on the testee 10 when the end point P1 of the biodegradable layer 120 intrudes into the subcutaneous layer 16 under the dermis 14. Accordingly, when both the end point P1 of the biodegradable layer 120 and the perpendicular surface S2 of the main body 110 are located in the region of the dermis 14, accurate biosignal data is obtained without inflicting pain to the testee 10. However, the present embodiment is not limited to the illustration of FIG. 6. For example, the end point P1 of the biodegradable layer 120 may intrude into the subcutaneous layer 16 of the testee 10, and the perpendicular surface S2 of the main body 110 may be located in the subcutaneous layer 16.

When a biosignal is measured in the region of the dermis 14, the length h2 of the biodegradable layer 120 is less than a thickness d2 of the dermis 14, and the length h1 of the main body 110 is greater than a thickness d1 of the epidermis 12. For example, the length h1 of the main body 110 is about 70 µm to about 1400 µm, and the length h2 of the biodegradable layer 120 is less than about 1330 µm. However, the present embodiment is not limited thereto. That is, the sizes of the biodegradable layer 120 and the main body 110 may vary according to the position where a biosignal is measured.

Figure 7:
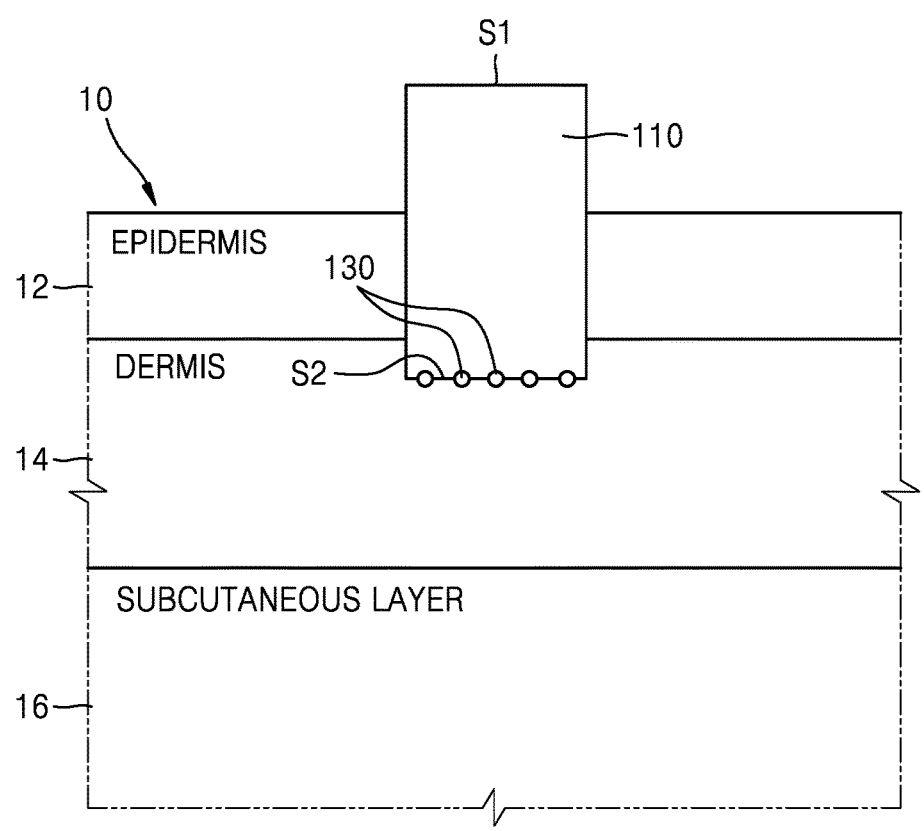
FIG. 7 is a cross-sectional view illustrating the biosensor needle of FIG. 6 after a biodegradable layer has decomposed.

FIG. 7 is a cross-sectional view illustrating the needle 100 of FIG. 6 after the biodegradable layer 120 has decomposed.

Referring to FIG. 7, the biodegradable layer 120 including a biodegradable polymer material decomposes in the skin of the testee 10, and the main body 110 contacts the dermis 14 of the testee 10. Then, the perpendicular surface S2 of the main body 110 contacts the dermis 14 of the testee 10. When the light is incident upon the incident surface S1 of the main body 110, the incident light is reflected from the region of the dermis 14 contacting the incident surface S1. The spectrum of the reflected light varies according to the types and amounts of materials included in interstitial fluid or blood distributed in the dermis 14. Accordingly, a distribution of materials of the interstitial fluid or blood distributed in the dermis 14 may be identified by analyzing the spectrum of the reflected light. Bioinformation such as blood sugar, cholesterol, a body fat amount of the testee 10 may be obtained from the distribution of materials of the interstitial fluid or blood. A disease of the testee 10 or whether the testee 10 is on medication may be diagnosed from the distribution of materials of the interstitial fluid or blood.

Figure 8:
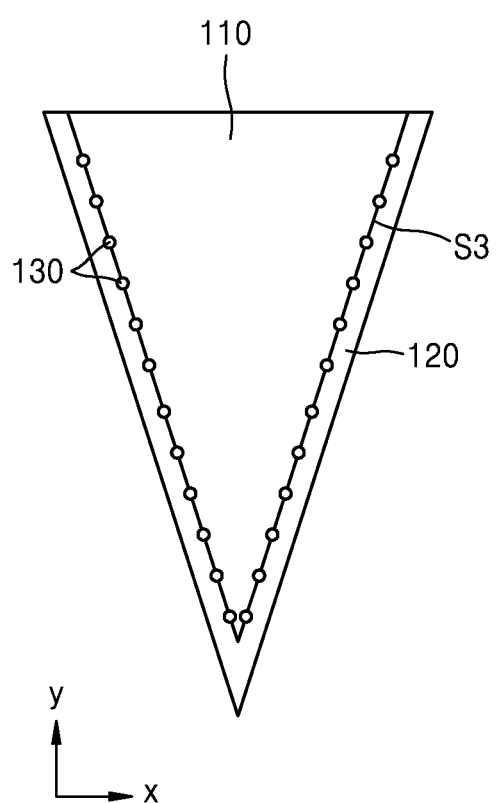
FIG. 8 is a cross-sectional view of a biosensor needle according to another embodiment of the present disclosure.

FIG. 8 is a cross-sectional view of the needle 100 according to another embodiment of the present disclosure.

Referring to FIG. 8, the main body 110 has a pointed shape. In other words, the main body 110 does not include the substantially perpendicular surface S2 that is substantially perpendicular to the length direction (y-axis) of the needle 100, but instead, includes the lateral surface S3 that is askew with respect to the length direction (y-axis) of the needle 100. The metal particles 130 are provided on the lateral surface S3 of the main body 110. The biodegradable layer 120 is coated on the lateral surface S3 of the main body 110. Accordingly, while the main body 110 is inserted into the skin of the testee 10, the metal particles 130 are prevented from being detached from the lateral surface S3 of the main body 110 due to friction with the skin.

The biodegradable layer 120 decomposes inside the testee 10. After the biodegradable layer 120 has decomposed, the lateral surface S3 contacts the skin of the testee 10. The light incident upon the main body 110 is reflected from the skin contacting the lateral surface S3. The metal particles 130 provided in the lateral surface S3 of the main body 110 enhance the Raman spectrum signal of the light reflected from the skin contacting the lateral surface S3 of the main body 110.

The embodiments of FIGS. 1 to 8 are directed to when the needle 100 includes the biodegradable layer 120. However, the present disclosure is not limited thereto. That is, the needle 100 may not include the biodegradable layer 120.

Figure 9:
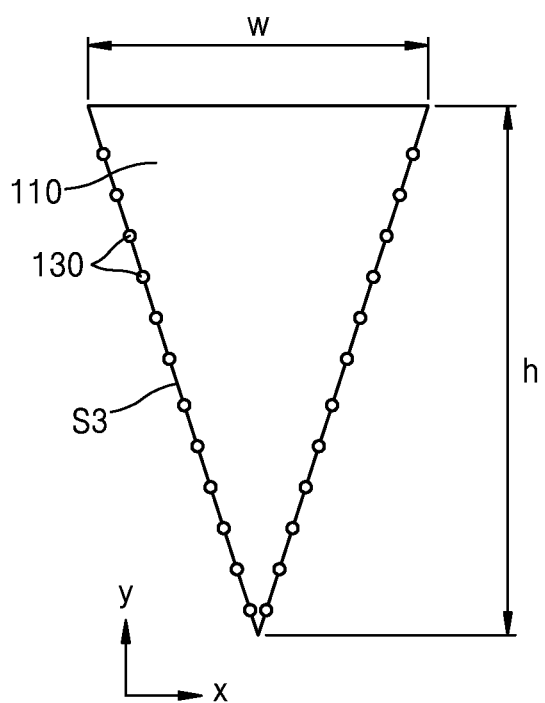
FIG. 9 is a cross-sectional view of a biosensor needle according to another embodiment of the present disclosure.

FIG. 9 is a cross-sectional view of the needle 100 according to another embodiment of the present disclosure.

Referring to FIG. 9, the needle 100 includes the main body 110 having a pointed shape and a width W less than the length h so as to be easily inserted into the testee 10. For example, the width W of the main body 110 is about 40 µm to about 60 µm, and the length h of the main body 110 is about 700 µm to about 1400 µm. However, the above values are merely examples, and the present embodiment is not limited thereto. The size of the main body 110 may vary according to the position where a biosignal is measured. For example, when a biosignal is measured in the subcutaneous layer 16 of the testee 10, the length h of the main body 110 is greater than about 1500 µm, and the width W of the main body 110 is greater than about 60 µm.

Figure 10:
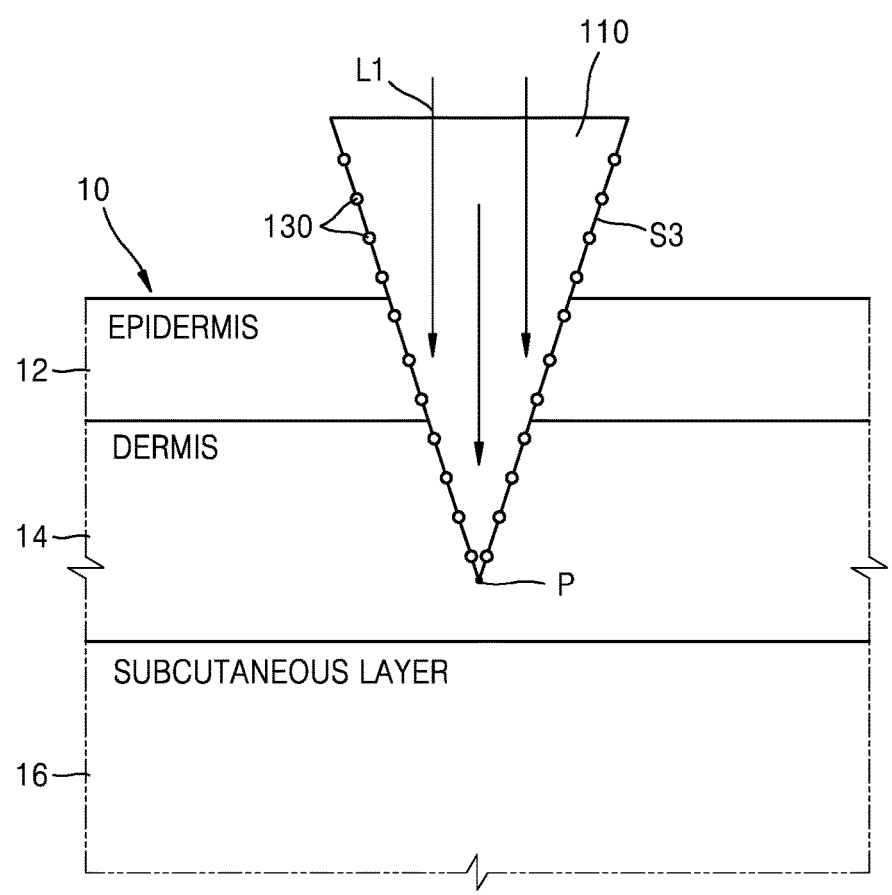
FIG. 10 is a cross-sectional view illustrating the biosensor needle of FIG. 9 inserted into a testee.

FIG. 10 is a cross-sectional view illustrating the needle 100 of FIG. 9 inserted into the testee 10.

Referring to FIG. 10, as the needle 100 is inserted into the testee 10, the lateral surface S3 of the main body 110 contacts the skin of the testee 10. FIG. 10 illustrates that the main body 110 is inserted into the dermis 14 of the testee 10. However, the present embodiment is not limited thereto. For example, the main body 110 is also insertable into the subcutaneous layer 16 of the testee 10. In the embodiment of FIG. 10, the lateral surface S3 of the main body 110 is askew to the length direction (y-axis) of the needle 100. The light incident upon the main body 110 is reflected from the skin of the testee 10 contacting the lateral surface S3 of the main body 110. The metal particles 130 provided on the lateral surface S3 of the main body 110 enhance the Raman spectrum signal of the light reflected from the skin of the testee 10 contacting the lateral surface S3 of the main body 110.

Figure 11:
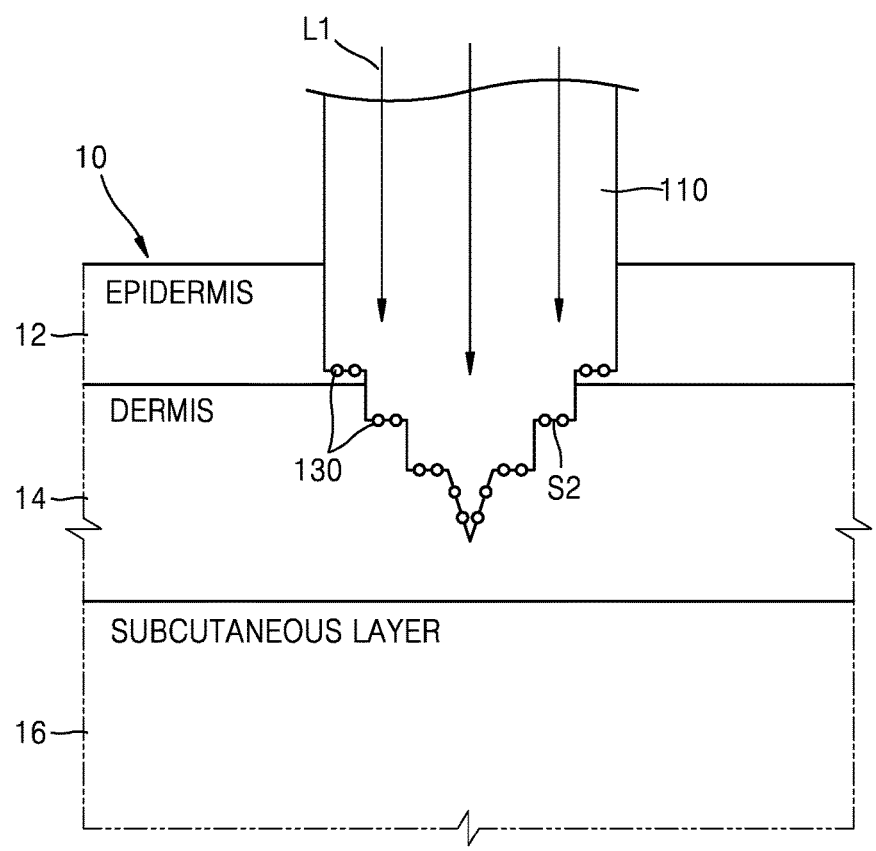
FIG. 11 is a cross-sectional view illustrating a biosensor needle inserted into a testee, according to another embodiment of the present disclosure.

FIG. 11 is a cross-sectional view illustrating the needle 100 inserted into the testee 10, according to another embodiment of the present disclosure.

Referring to FIG. 11, the needle 100 includes the main body 110 and the metal particles 130 provided at least a part of the main body 110. The main body 110 includes at least one surface S2 that is substantially perpendicular to the length direction (y-axis) of the needle 100. When the section of the main body 110 is configured as illustrated in FIG. 11, the incident direction of the incident light L1 and the substantially perpendicular surface S2 of the main body 110 contacting the skin are substantially perpendicular to each other.

In general, the strength of a Raman spectrum signal is at a maximum when a light reflection surface and a light incident direction are substantially perpendicular to each other. Accordingly, as illustrated in FIG. 10, when an incident direction of the incident light L1 is askew to a reflection surface, the Raman spectrum signal of the reflected light may be relatively weak. To address this matter, the main body 110 of FIG. 11 includes at least one surface S2 that is substantially perpendicular to the length direction (y-axis) of the needle 100. To facilitate intrusion of the needle 100 into the skin, the main body 110 has a structure in which the substantially perpendicular surfaces S2 are connected in a step form. When the main body 110 is configured as illustrated in FIG. 11, the incident light L1 and the reflection surface where the incident light L1 is reflected from the skin are substantially perpendicular to each other, and thus, the strength of a Raman spectrum signal may be enhanced. Since the substantially perpendicular surfaces S2 are connected in a step form, the main body 110 may be easily inserted into the skin.

Figure 12:
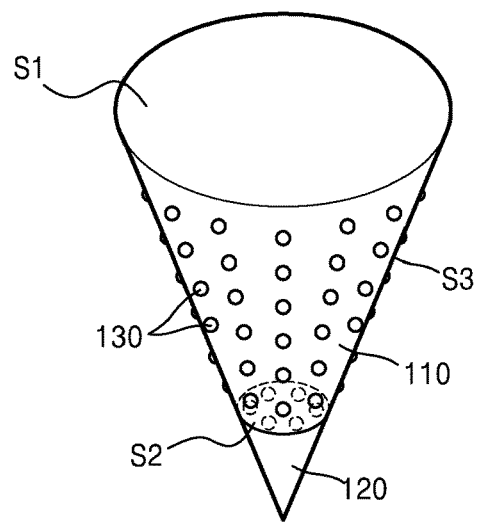
FIG. 12 is a perspective view illustrating the shape of the biosensor needle of FIG. 1.

FIG. 12 is a perspective view illustrating the shape of the needle 100 of FIG. 1.

Referring to FIG. 12, the needle 100 has a conic shape in which the main body 110 has a shape of a circular column having an area of the substantially perpendicular surface S2 that is less than an area of the incident surface S1. The metal particles 130 are provided on the substantially perpendicular surface S2 and the lateral surface S3 of the main body 110. The metal particles 130 may also be provided in an interior of the main body 110. The biodegradable layer 120 includes a biodegradable polymer material, has a conic shape, and is attached on the substantially perpendicular surface S2 of the main body 110. Although FIG. 12 illustrates when the main body 110 has a circular column shape, the present embodiment is not limited thereto.

Figure 13:
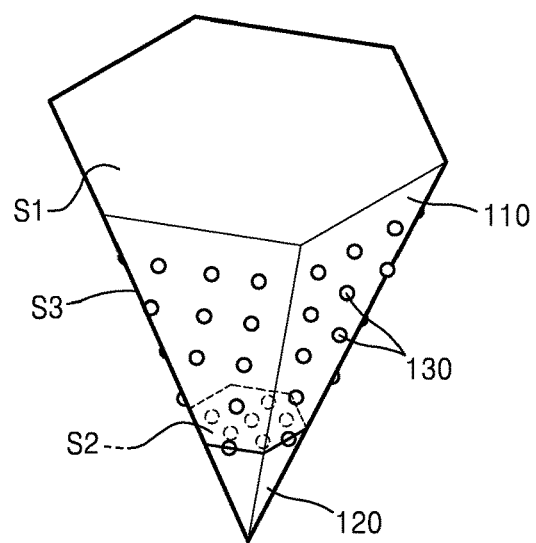
FIG. 13 is a perspective view illustrating an example of another shape of the biosensor needle of FIG. 1.

FIG. 13 is a perspective view illustrating an example of another shape of the needle 100 of FIG. 1.

Referring to FIG. 13, the needle 100 has a shape of a polypyramid, and a bottom surface of the polypyramid is hexagonal. However, the present embodiment is not limited thereto, and the bottom surface of a polypyramid may also have a polygonal shape. In FIG. 13, the main body 110 has a shape of a polygonal column. The incident surface S1 and the substantially perpendicular surface S2 of the main body 110 have polygonal shapes. The biodegradable layer 120 has a polypyramid shape. When the needle 100 is inserted into the skin of the testee 10, the biodegradable layer 120 decomposes, and at least a part of the substantially perpendicular surface S2 and the lateral surface S3 of the main body 110 contact the skin of the testee 10. The metal particles 130 are provided on the surface of the main body 110 and in the main body 110.

The shapes of the needle 100 of FIGS. 12 and 13 are not limited thereto, and the needle 100 may have a different shape of a sharp end than the shapes of FIGS. 12 and 13. Furthermore, FIGS. 12 and 13 illustrate when a section of the needle 100 has the shape of FIG. 1. However, the shape of the section of each of the needles 100 of FIGS. 12 and 13 may have a different shape. For example, the biodegradable layer 120 may cover not only the substantially perpendicular surface S2 of the main body 110, but also the lateral surface S3 of the main body 110. The biodegradable layer 120 may not be included in the needle 100, and a tip end of the main body 110 may have a pointed shape.

Figure 14:
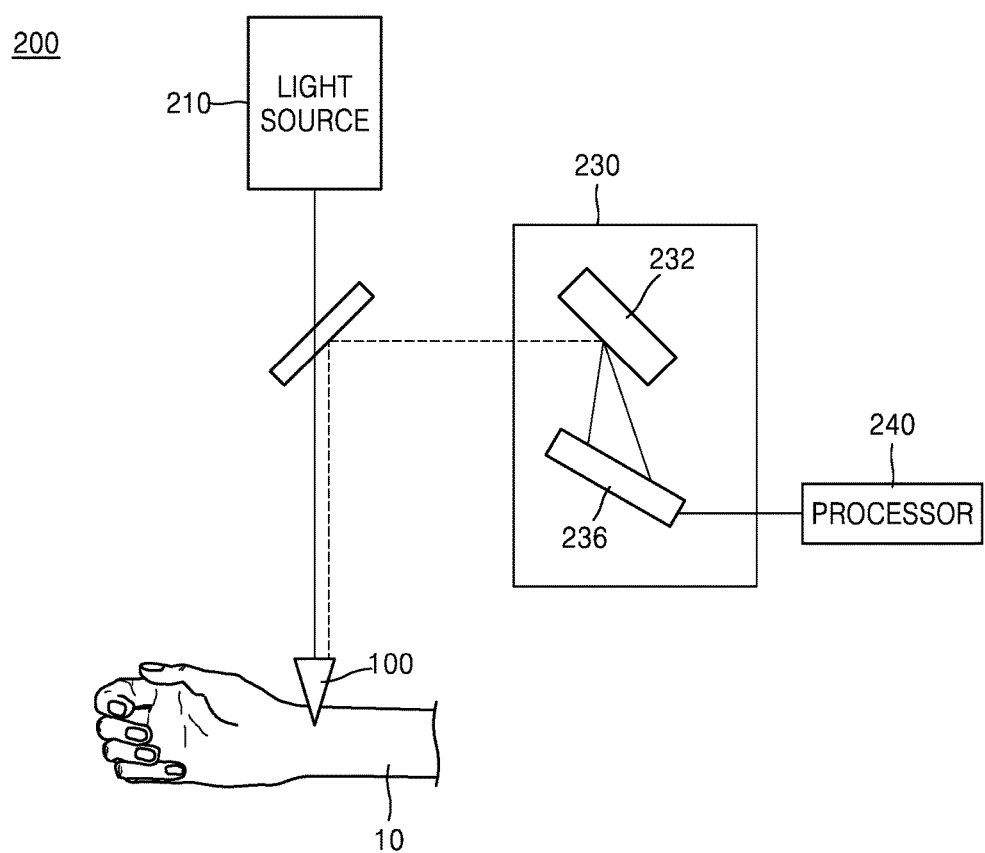
FIG. 14 schematically illustrates a biosensor according to an embodiment of the present disclosure.

FIG. 14 schematically illustrates a biosensor 200 according to an embodiment of the present disclosure.

Referring to FIG. 14, the biosensor 200 includes the needle 100. All of the above-described embodiments described with reference to FIGS. 1 to 13 may be applied to the needle 100 of FIG. 13. The biosensor 200 further includes a light source 210. Light output from the light source 210 may be incident upon the needle 100 and has a wavelength of about 700 μm to about 1400 μm. In other words, light has a wavelength of a region of red light to near infrared (NIR), and thus a Raman spectrum signal is more efficiently obtained from the skin of the testee 10 since molecular structures of the materials included in interstitial fluid or blood of a living body absorb and scatter light of this wavelength range. However, the present disclosure is not limited thereto, and the light source 210 may output light having a different wavelength according to a type of a target material.

The biosensor 200 further includes a spectrum measurement unit 230 that measures a spectrum of the light reflected from the skin of the testee 10 via the needle 100, and a processor 240 that determines bioinformation of the testee 10 by processing a spectrum of a reflected light signal measured by the spectrum measurement unit 230. The bioinformation of the testee 10 includes information related to the distribution of materials included inside the testee 10, and includes a health state or a metabolism state of the testee 10 which may be identified from the distribution of materials included in the skin of the testee 10.

The spectrum measurement unit 230 outputs a distribution of strength for each wavelength of the reflected light. For example, the spectrum measurement unit 230 includes a spectrometer 232 for splitting a reflected light for each wavelength and a sensor 236 for measuring strength of the light split by the spectrometer 232. The spectrometer 232 may have a grating structure. When the reflected light is incident upon the spectrometer 232 having a grating structure, the reflected light may travel along a different path according to the wavelength of the reflected light. However, the present embodiment is not limited thereto, and the spectrum measurement unit 230 may include a plurality of light receiving sensors which are each provided with a light filter corresponding to a certain wavelength. In addition, the spectrum measurement unit 230 may be implemented in a different structure capable of measuring a distribution of strength of the reflected light according to the wavelength of the reflected light.

The processor 240 determines information about the types and amounts of the materials included in the skin of the testee 10 from the spectrum of the reflected light measured by the spectrum measurement unit 230. For example, the processor 240 identifies a Raman shift occurring in the skin of the testee 10 by comparing the spectrum of the reflected light and the spectrum of the incident light. The processor 240 determines information about the types of the materials included inside the testee 10 from the Raman shift value. For example, the interstitial fluid or blood of the testee 10 includes glucose, urea, ceramide, keratin, or collagen. Glucose has a Raman shift value as large as a wavenumber ($cm^{-1}$) of about 436.4 $cm^{-1}$, 1065 $cm^{-1}$, 1126.4 $cm^{-1}$, or 525.7 cm$^{-1}$. Collagen has a Raman shift value of about 855 cm$^{-1}$ or 936 cm$^{-1}$. Urea has a Raman shift value of about 1000 cm$^{-1}$.

The processor 240 identifies a distribution amount of each material from the strength of a spectrum peak at a position where the frequency of the incident light is shifted as much as a Raman shift value corresponding to each material from the wavelength of the reflected light. For example, a distribution amount of glucose may be as large as the strength of a spectrum peak at a position where a wavelength is shifted from a wavenumber of the incident light as much as about 436.4 cm$^{-1}$, 1065 cm$^{-1}$, 1126.4 cm$^{-1}$, or 525.7 cm$^{-1}$. A distribution amount of collagen may be as large as the strength of a spectrum peak at a position where a wavelength is shifted from a wavenumber of the incident light as much as about 855 cm$^{-1}$ or 936 cm$^{-1}$. In order to quantitatively determine the amount of a material from the strength of a spectrum peak, the processor 240 stores a lookup table about a correlation between the amount of a material and a spectrum peak value. The processor 240 diagnoses a health state of the testee 10 from the amount of a distribution of materials in the skin of the testee 10.

The processor 240 outputs information about whether a harmful material is included in the skin of the testee 10. For example, the processor 240 identifies, from the spectrum of the reflected light, whether dermatophytosis germs such as trichophyton mentagrophytes or trichophyton rubrum, or basal cell epithelioma, squamous cell carcinoma, or skin cancer cells such as melanoma, are included in the skin of the testee 10. The processor 240 identifies, from the spectrum of the reflected light, whether drugs such as morphine, cocaine, or philopon are included in the skin of the testee 10. The skin cancer cells, germs, and drugs have Raman shift values different from those of the above-described normal metabolism materials such as collagen, glucose, or urea. Accordingly, the processor 240 determines information about whether the testee 10 may have a drug addiction or processes a disease gene by observing a position where a spectrum peak appears in the spectrum of the reflected light.

FIG. 14 illustrates when the biosensor 200 includes one needle 100. However, the present embodiment is not limited thereto. For example, the biosensor 200 may include a plurality of needles 100 to which the light source 210 may output light.

When the biosensor 200 measures the spectrum signal of the reflected light by using only the needle 100, as illustrated in FIG. 14, other external factors in addition to the bioinformation of the testee 10 may be involved. For example, when the strength of the light output from the light source 210 is not constant, even when there is no change in the bioinformation of the testee 10, the strength of the light reflected from the skin of the testee 10 may vary, and the spectrum signal of the reflected light may vary by a change in the depth or direction in which the needle 100 is inserted into the skin of the testee 10.

Figure 15A:
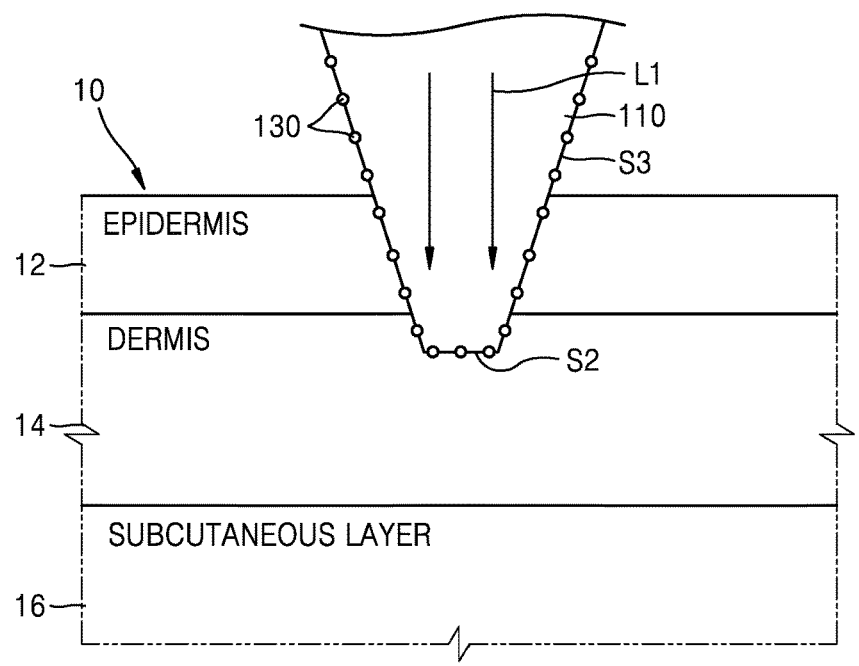
FIGS. 15A and 15B illustrate states in which the biosensor needle of FIG. 1 is inserted into skin of a testee.
Figure 15B:
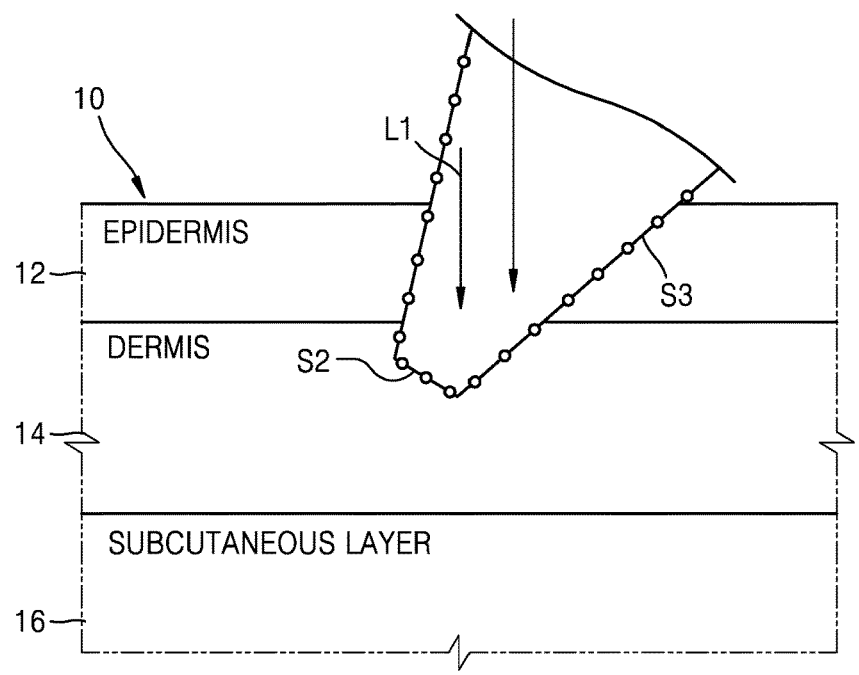

FIGS. 15A and 15B illustrate states in which the needle 100 of FIG. 1 is inserted into the skin of the testee 10.

FIG. 15A illustrates that the main body 110 of the needle 100 stands upright with respect to the skin of the testee 10. In this case, the incident light L1 and the substantially perpendicular surface S2 of the main body 110 are substantially perpendicular to each other. In contrast, FIG. 15B illustrates when the main body 110 stands askew in the skin of the testee 10. Thus, an area where the main body 110 and the skin of the testee 10 contact each other varies between FIGS. 15A and 15B.

In addition, in FIG. 15B, the incident direction of the incident light L1 and the substantially perpendicular surface S2 of the main body 110 are not substantially perpendicular to each other, and an angle between the lateral surface S3 of the main body 110 and the incident direction of the incident light L1 varies. The spectrum signal of the reflected light varies by a change in the incident angle of the incident light L1 with respect to the main body 110 and in a contact area between the main body 110 and the skin of the testee 10. Accordingly, in order to improve reliability in the measurement of a biosignal, the change in the spectrum signal of the reflected light due to the above-described factors needs to be corrected.

Figure 16:
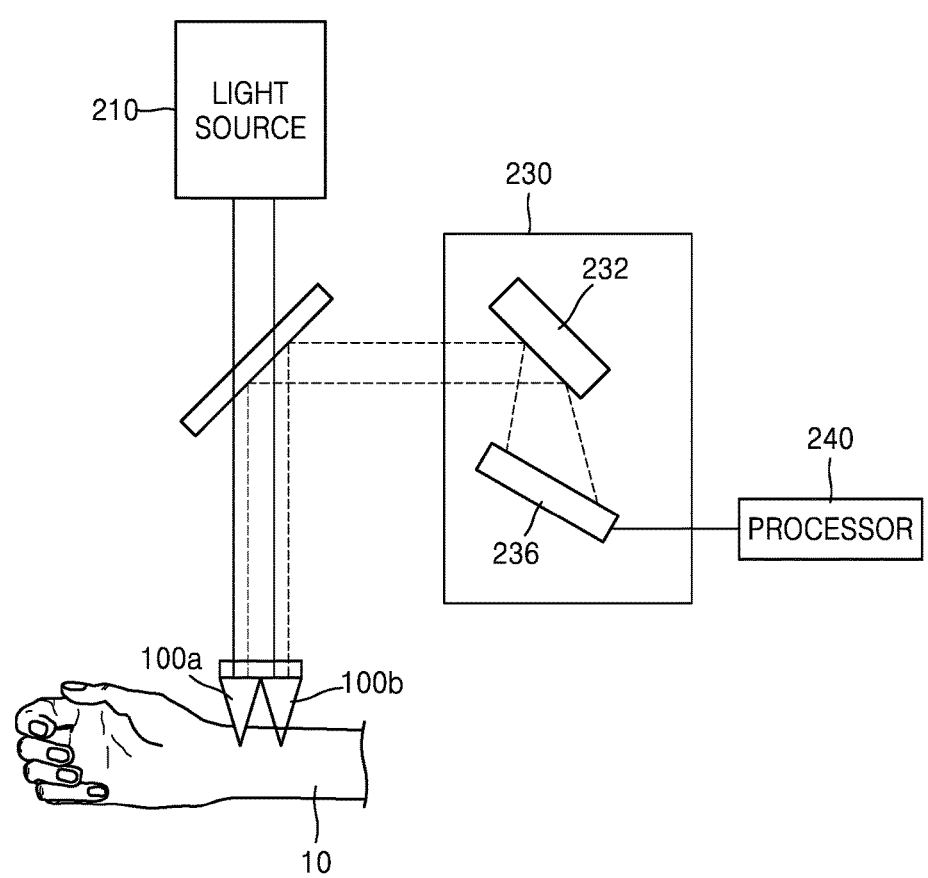
FIG. 16 schematically illustrates a biosensor according to another embodiment of the present disclosure.

FIG. 16 schematically illustrates the biosensor 200 according to another embodiment of the present disclosure. In the description of the embodiment of FIG. 16, a redundant description of the embodiment of FIGS. 15A and 15B is omitted for conciseness.

Referring to FIG. 16, the biosensor 200 includes a needle 100a and an auxiliary needle 100b. The needle 100a and the auxiliary needle 100b are insertable together into the skin of the testee 10. The light output from the light source 210 may be incident upon the needle 100a and the auxiliary needle 100b. The spectrum measurement unit 230 simultaneously or separately measures a spectrum of the reflected light from the needle 100a and a spectrum of the reflected light from the auxiliary needle 100b. In other words, although FIGS. 15A and 15B illustrate when one spectrum measurement unit 230 is provided to measure the spectrum of the reflected light from both the needle 100a and the needle 100b altogether, the present embodiment is not limited thereto. For example, a plurality of spectrum measurement units 230 may be provided to separately analyze the spectrum of the reflected light from the needle 100a and the spectrum of the reflected light from the auxiliary needle 100b.

Figure 17:
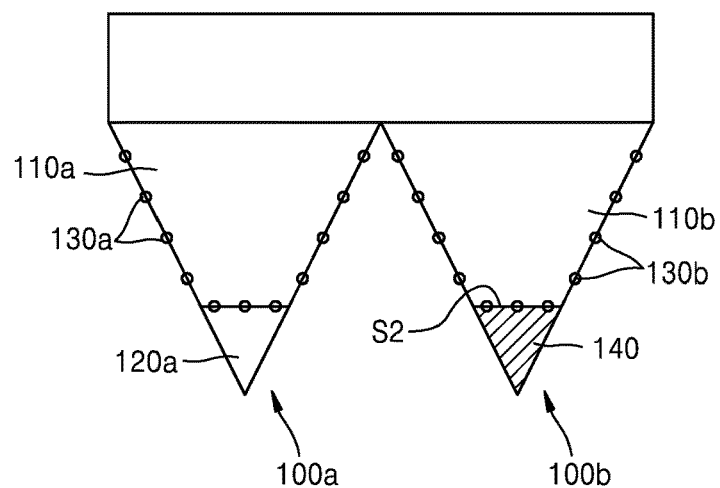
FIG. 17 is a cross-sectional view of the biosensor needle and an auxiliary needle of the a biosensor of FIG. 16.

FIG. 17 is an enlarged cross-sectional view of the needle 100a and the auxiliary needle 100b of FIG. 16.

Referring to FIG. 17, the needle 100a includes a first main body 110a, a plurality of first metal particles 130a, and a first biodegradable layer 120a. However, the present disclosure is not limited thereto. For example, all embodiments described with reference to FIGS. 1 to 13 may be applied to the needle 100a.

The auxiliary needle 100b includes a second main body 110b and a reference layer 140 attached on at least a part of a surface of the second main body 110b. The auxiliary needle 100b includes a plurality of second metal particles 130b provided at least a part of the second main body 110b. The light output from the light source 210 of FIGS. 15A and 15B may be incident upon the second main body 110b. Unlike the needle 100a, the light incident upon the second main body 110b of the auxiliary needle 100b is reflected from the reference layer 140. In other words, the light incident upon the auxiliary needle 100b is reflected not from the skin of the testee 10, but from the reference layer 140. Accordingly, the spectrum of the reflected light from the auxiliary needle 100b is dependent on the reference layer 140 instead of the bioinformation of the testee 10. A Raman spectrum signal of the reference layer 140 may be already known. Accordingly, when a spectrum signal is measured, a Raman spectrum signal of the reference layer 140 may be easily identified. As described below, the Raman spectrum signal of the light reflected from the skin of the testee 10 may be corrected based on the strength of the Raman spectrum signal of the reference layer 140.

The reference layer 140 includes a material such as polyacrylic acid (PAA), Rhodamine 6G, 4-Aminobenzoic acid, 4-Mercaptobenzoic acid, pyridine, polyvinyl acetate, polyamide, polyethylene, or polytiophene, all having a superior SERS effect. Accordingly, when the reference layer 140 includes the above materials, the spectrum of the light reflected from the reference layer 140 may be easily measured. The materials may not be generally included in the skin of a living body. Accordingly, the reference layer 140 has a Raman shift value that is different from that of the skin of the testee 10. Accordingly, even when the spectrum measurement unit 230 simultaneously measures the spectrum of the reflected light from the needle 100*a* and the auxiliary needle 100*b*, a peak of the spectrum of the reflected light from the auxiliary needle 100*b* may be easily identified. However, the present embodiment is not limited to these materials for the reference layer 140.

The second metal particles 130*b* are provided on a contact surface between the second main body 110*b* and the reference layer 140, and include at least one of gold (Au) particles, silver (Ag) particles, and copper (Cu) particles. However, the present disclosure is not limited thereto. The second metal particles 130*b* enhance the spectrum signal of the light reflected from the reference layer 140.

Referring back to FIG. 16, the spectrum measurement unit 230 of the biosensor 200 measures the spectrum of the reflected light from the needle 100*a* and the auxiliary needle 100*b*. The processor 240 of the biosensor 200 normalizes the spectrum of the reflected light from the needle 100*a* and from the auxiliary needle 100*b*. In other words, the processor 240 normalizes the spectrum signal of the light reflected from the skin of the testee 10 from the spectrum signal of the light reflected from the reference layer 140.

As described above, the spectrum of the light reflected from the reference layer 140 may not be dependent upon the testee 10. Nevertheless, the strength of the spectrum of the light reflected from the reference layer 140 may be changed by noise generation factors such as a change in the strength of the light output from the light source 210 and the depth or angle of insertion of the auxiliary needle 100*b*. Accordingly, whether the above-described noise generation factors are involved may be identified from a change in the spectrum of the light reflected from the reference layer 140. When the processor 240 normalizes the spectrum signal of the light reflected from the skin of the testee 10 from the spectrum signal of the light reflected from the reference layer 140, bioinformation of the testee 10 may be obtained from a normalized signal with high reliability.

For example, the processor 240 normalizes a peak value of the spectrum of the light reflected from the skin of the testee 10 through the following Equation (1).

$$A' = A/B \quad (1)$$

In Equation (1), A denotes a peak value of the spectrum of the light reflected from the skin of the testee 10, and B denotes a peak value the spectrum of the light reflected from the reference layer 140. Furthermore, A' denotes a normalized value the peak of the spectrum of the light reflected from the skin of the testee 10. When normalization is performed through Equation (1), even when the value A is changed by the above-described noise generation factors, the change may be compensated for by a change of the value B.

For example, when the value A is changed as the light irradiation strength of the light source 210 decreases, as the value B decreases at about the same rate, the normalized value A' may not be changed by the above-described noise generation factors. In another example, even when a pressure applied to the needle 100*a* is changed, thereby changing the value A, a pressure applied to the auxiliary needle 100*b* located nearby is also changed, which changes the value B. Accordingly, since the change of the value A is compensated for by the change in the value B, the normalized value of A' may not be changed by the above-described noise generation factors of the testee 10. In another example, an angle at which the needle 100*a* is inserted into the skin of the testee 10 may be changed. In this state, if the needle 100*a* and the auxiliary needle 100*b* are provided in a package, an angle at which the auxiliary needle 100*b* is inserted into the skin of the testee 10 may also vary. Accordingly, as the change in the value A is compensated for by the change in the value B, the normalized value of A' may not be changed by the above-described noise generation factors of the testee 10.

Equation (1) is an example, and the present embodiment is not limited thereto. When the value A is changed by a noise factor, the normalization may be performed by another method of compensating for the change in the value A based on the change in the value B due to the same factor. When the spectrum signal of the light reflected from the skin of the testee 10 is normalized, the processor 240 may output the bioinformation of the testee 10 based on a normalized spectrum signal. The output bioinformation includes information about a distribution of the materials included in the skin of the testee 10, a health state of the testee 10, whether the testee 10 has a disease, or whether the testee 10 is on medication, which may be analogized from the distribution of the materials included in the skin of the testee 10.

In FIG. 17, a section of the second main body 110*b* has a trapezoidal shape, and a section of the reference layer 140 has a triangular shape. When the auxiliary needle 100*b* is manufactured as illustrated in FIG. 17, the surface S2 of the second main body 110*b* is substantially perpendicular to the incident direction of the incident light. Accordingly, the spectrum signal strength of the light reflected from the reference layer 140 attached on the substantially perpendicular surface S2 of the second main body 110*b* increases. However, the section of the auxiliary needle 100*b* may vary.

Figure 18:
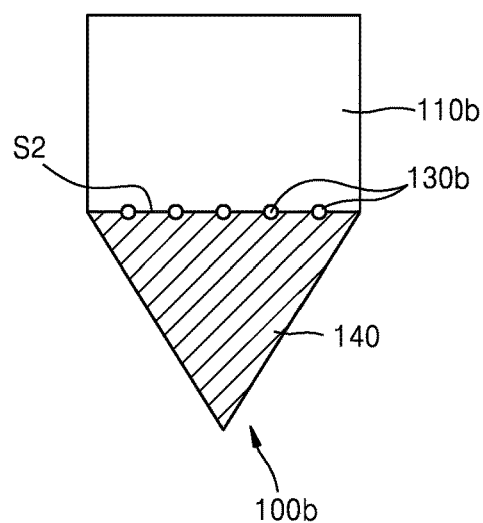
FIGS. 18 and 19 are cross-sectional views of auxiliary needles according to embodiments of the present disclosure.
Figure 19:
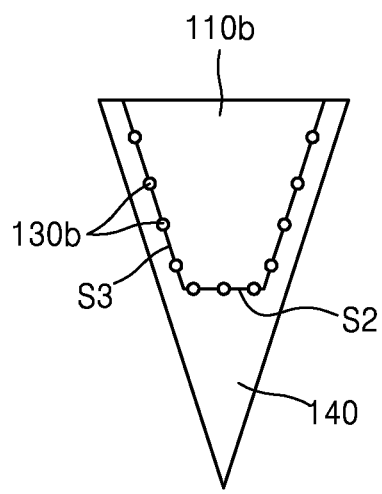

FIGS. 18 and 19 are cross-sectional views of the auxiliary needles 100*b* according to other embodiments of the present disclosure.

Referring to FIG. 18, a section of the second main body 110*b* has a rectangular shape and a section of the reference layer 140 has a triangular shape. Since a tip end of the reference layer 140 has a pointed shape, the reference layer 140 may be easily inserted into the skin of the testee 10. The substantially perpendicular surface S2 of the second main body 110*b* may be substantially perpendicular to the incident direction of the incident light. The second metal particles 130*b* are provided at least a part of the second main body 110*b* so as to enhance the spectrum signal of the light reflected from the reference layer 140. The second metal particles 130*b* are provided inside the second main body 110*b* or on another surface of the second main body 110*b*.

Referring to FIG. 19, the section of the second main body 110*b* has a trapezoidal shape. The reference layer 140 covers not only the substantially perpendicular surface S2 of the second main body 110*b*, but also at least a part of the lateral surface S3. The metal particles 130 are provided on the substantially perpendicular surface S2 and the lateral surface S3 of the second main body 110*b*, and are provided inside the second main body 110*b* or on another surface of the second main body 110*b*. As illustrated in FIG. 19, when a contact area between the second main body 110*b* and the reference layer 140 increases, the spectrum signal strength of the light reflected from the reference layer 140 also increases.

Figure 20:
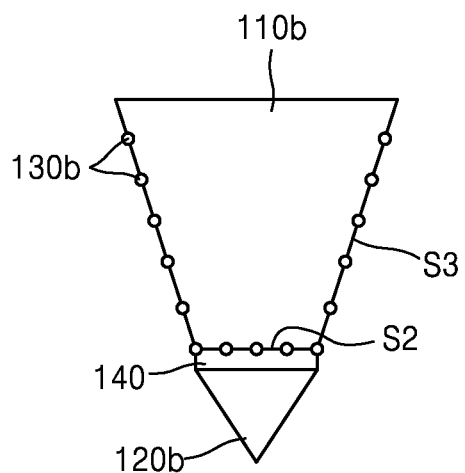
FIGS. 20, 21 and 22 are cross-sectional views of auxiliary needles according to embodiments of the present disclosure.
Figure 21:
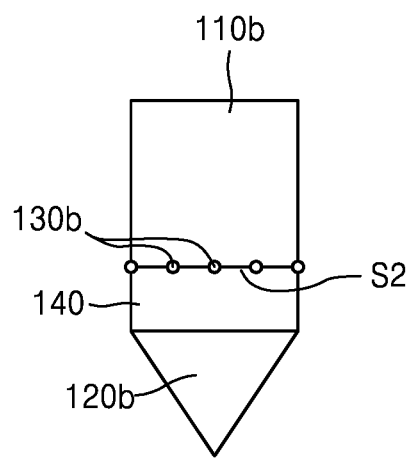
Figure 22:
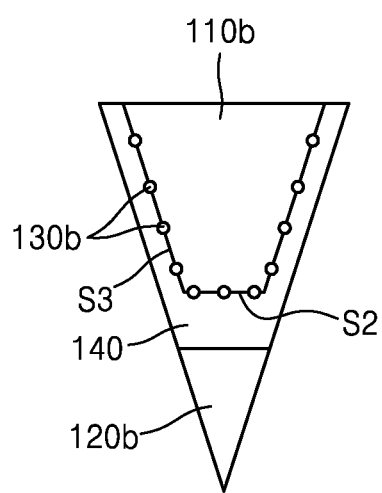

FIGS. 20 to 22 are cross-sectional views of the auxiliary needles 100b according to other embodiments of the present disclosure.

Each of the auxiliary needles 100b of FIGS. 20 to 22 includes a second biodegradable layer 120b including a biodegradable polymer material, such as at least one of polylactic acid, poly(lactic-co-glycolic) acid, poly(caprolactone), polyhydroxyalkanoates, poly(propylene fumarate), polydioxanone, polyglycolide, polyanhydrides, polyacetals, poly(ortho esters), polycarbonates, polyurethanes, and polyphosphazenes. However, the present disclosure is not limited thereto. The second biodegradable layer 120b decomposes in the skin of the testee 10, thereby reducing a skin insertion length of the auxiliary needle 100b.

Referring to FIGS. 20 and 21, the reference layer 140 is coated on the substantially perpendicular surface S2 of the second main body 110b. A coating thickness of the reference layer 140 varies according to the size of a desired reference signal. As illustrated in FIGS. 20 and 21, a section of the second main body 110b may have a trapezoidal shape, a rectangular shape, or other shapes. The second biodegradable layer 120b is attached on a lower surface of the reference layer 140. The second metal particles 130b are provided on at least a part of the second main body 110b, and enhance the spectrum signal of the light reflected from the reference layer 140. The second biodegradable layer 120b is attached on the lower surface of the reference layer 140. A tip end of the second biodegradable layer 120b has a pointed shape. Accordingly, the second biodegradable layer 120b is easily inserted into the skin of the testee 10. Since the second biodegradable layer 120b is decomposable in the skin of the testee 10, the testee 10 does not experience pain from a sharp portion of the second biodegradable layer 120b.

Referring to FIG. 22, the reference layer 140 covers the lateral surface S3 of the second main body 110b. As the contact area between the reference layer 140 and the second main body 110b increases, the spectrum signal strength of the light reflected from the reference layer 140 also increases. The second biodegradable layer 120b is attached on the lower surface of the reference layer 140. A tip end of the second biodegradable layer 120b has a pointed shape. Accordingly, the second biodegradable layer 120b is easily inserted into the skin of the testee 10. Since the second biodegradable layer 120b is decomposable in the skin of the testee 10, the testee 10 does not experience pain from a sharp portion of the second biodegradable layer 120b.

Referring back to FIG. 16, the biosensor 200 is described as including one needle 100a and one auxiliary needle 100b. However, the present disclosure is not limited thereto. For example, the biosensor 200 may include a plurality of needles 100a and a plurality of auxiliary needles 100b, by which the biosensor 200 may measure a biosignal by inserting a plurality of needles into the skin of the testee 10, as will now be described.

Figure 23:
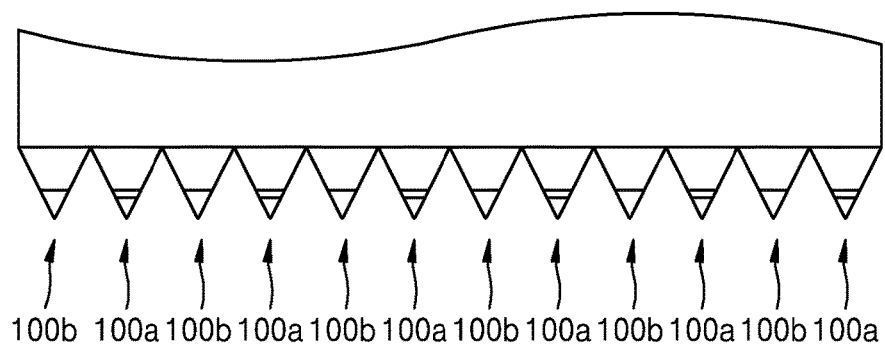
FIGS. 23 and 24 are cross-sectional views illustrating arrangements of a plurality of needles for a biosensor and a plurality of auxiliary needles of the biosensor.
Figure 24:
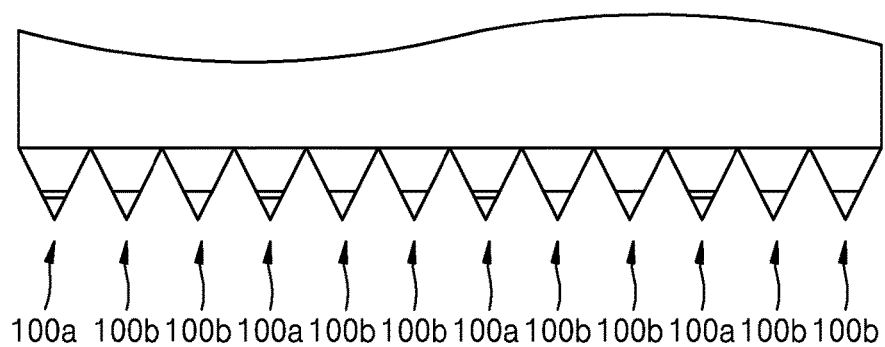

FIGS. 23 and 24 are cross-sectional views illustrating arrangements of a plurality of needles 100a and a plurality of auxiliary needles 100b of the biosensor 200.

Referring to FIG. 23, the biosensor 200 includes a plurality of needles 100a and a plurality of auxiliary needles 100b, wherein the needles 100a are arranged at even-numbered positions and the auxiliary needles 100b are arranged at odd-numbered positions. Referring to FIG. 24, the needles 100a are arranged at 3n-th and (3n+2)th positions, where n is 0 or a natural number, and the auxiliary needles 100b are arranged at (3n+1)th positions, where n is 0 or a natural number. However, the present embodiment is not limited thereto. For example, the ratio and arrangement order between the number of the needles 100a and the number of the auxiliary needles 100b may vary.

According to the above-described embodiments, a biosensor needle having a needle shape is inserted into the skin of the testee 10, and the spectrum of the light reflected from the skin of the testee 10 may be obtained. As a result, reliability of a biosignal is improved compared to obtaining a biosignal from the surface of the skin of the testee 10. As the metal particles 130 are inserted into at least a part of the main body 110, the spectrum signal of the reflected light is enhanced. As a result, even when the needle 100 or 100a is manufactured to be small, the spectrum signal strength of the reflected light increases. A reflected light signal of the needle 100 or 100a is normalized by using the auxiliary needle 100b, thereby reducing an error due to other noise factors than a change in the bioinformation of the testee 10.

The needle 100 or 100a and the biosensor 200 according to the above-described embodiments may be applied to various fields so as to provide a healthcare function by being combined with medical apparatuses or wearable apparatuses.

It should be understood that embodiments described herein should be considered in a descriptive sense only and not for purposes of limitation. Descriptions of features or aspects within each embodiment should typically be considered as available for other similar features or aspects in other embodiments of the present disclosure.

While one or more embodiments have been described with reference to the figures, it will be understood by those of ordinary skill in the art that various changes in form and details may be made therein without departing from the spirit and scope of the present disclosure as defined by the following claims.

What is claimed is:

1. A biosensor needle comprising:
a light-transmissive main body having a width that is less than a length of the main body, and is insertable into a testee; and
a plurality of metal particles provided on at least a portion of only an outer surface of the main body configured to contact a testee and generating a surface enhanced Raman scattering effect of light incident through the main body.

2. The biosensor needle of claim 1, wherein the plurality of metal particles comprises at least one of gold particles, silver particles, and copper particles.

3. The biosensor needle of claim 1, wherein the main body comprises a transparent polymer material.

4. The biosensor needle of claim 3, wherein the transparent polymer material is obtained by polymerizing at least one monomer of aniline, EDOT(3,4-ethylenedioxythiophene), pyrrole, N-succinimidyl acrylate, acrylamide, thiophene, aniline-co-pyrrole, amylopectin, carboxymethyl cellulose, dialcohol dimethyl quaterthiophene-co-adipic acid, and methylvinylether/maelic anhydride+ethyleneglycol.

5. The biosensor needle of claim 1, further comprising a biodegradable layer attached onto at least a portion of the surface of the main body and comprising a biodegradable polymer material.

6. The biosensor needle of claim 5, wherein a first end of the biodegradable layer contacts the main body and a second end of the biodegradable layer has a sharp, pointed shape.

7. The biosensor needle of claim 5, wherein the plurality of metal particles are disposed between the biodegradable layer and the main body.

8. The biosensor needle of claim 5, wherein the biodegradable polymer material comprises at least one of polylactic acid, poly(lactic-co-glycolic) acid, poly(caprolactone), polyhydroxyalkanoates, poly(propylene fumarate), polydioxanone, polyglycolide, polyanhydrides, polyacetals, poly(ortho esters), polycarbonates, polyurethanes, and polyphosphazenes.

9. The biosensor needle of claim 5, wherein the main body comprises at least one surface substantially perpendicular to a length direction of the needle.

10. The biosensor needle of claim 9, wherein the biodegradable layer is attached on a surface of the main body that is substantially perpendicular to the length direction of the needle.

11. The biosensor needle of claim 1, wherein the width of the main body is about 40 microns (μm) to about 60 μm and the length of the main body is about 700 μm to about 1400 μm.

* * * * *